United States Patent [19]

Yanagihara et al.

[11] 4,409,947
[45] Oct. 18, 1983

[54] EXHAUST GAS RECIRCULATING TYPE DIESEL ENGINE

[75] Inventors: Hiromichi Yanagihara; Noriyuki Tokoro, both of Gotenba, Japan

[73] Assignee: Toyota Jidosha Kabushiki Kaisha, Toyota, Japan

[21] Appl. No.: 232,175

[22] Filed: Feb. 6, 1981

[30] Foreign Application Priority Data

| Sep. 4, 1980 [JP] | Japan | 55-121703 |
| Sep. 4, 1980 [JP] | Japan | 55-125010[U] |
| Sep. 5, 1980 [JP] | Japan | 55-125530[U] |

[51] Int. Cl.³ ............................................. F02M 25/06
[52] U.S. Cl. ................. 123/569; 123/193 P; 92/214; 92/175
[58] Field of Search ............. 123/569, 193 P; 92/214, 92/175

[56] References Cited

U.S. PATENT DOCUMENTS

| Re. 21,750 | 3/1941 | Starr | 123/569 |
| 3,542,376 | 11/1970 | Dykehouse | 277/58 |
| 3,704,893 | 12/1972 | Hill | 277/171 |
| 3,834,719 | 9/1974 | Shin et al. | 277/170 |
| 3,965,872 | 6/1976 | Taira | 123/193 P |
| 4,020,809 | 5/1977 | Kern | 123/569 |
| 4,123,072 | 10/1978 | Sharpe | 277/216 |
| 4,138,125 | 2/1979 | Lucas | 277/170 |
| 4,282,837 | 8/1981 | Holtman et al. | 123/193 P |
| 4,346,685 | 8/1982 | Fujikawa | 123/193 P |

FOREIGN PATENT DOCUMENTS

| 2166443 | 2/1971 | Fed. Rep. of Germany ... 123/193 P |
| 1221287 | 2/1971 | United Kingdom . |
| 1232527 | 5/1971 | United Kingdom . |
| 2002874 | 2/1979 | United Kingdom . |
| 2028464 | 3/1980 | United Kingdom ............ 123/193 P |

Primary Examiner—Wendell E. Burns
Attorney, Agent, or Firm—Kenyon & Kenyon

[57] ABSTRACT

An exhaust gas recirculating type diesel engine wherein part of the exhaust gas is recirculated from its exhaust system to its intake system. An annular groove is formed on the circumferential surface of the piston, and a ring for preventing small particles generated within the combustion chamber from being transferred is engaged within the annular groove.

8 Claims, 20 Drawing Figures

EXHAUST GAS RECIRCULATING TYPE DIESEL ENGINE

BACKGROUND OF THE INVENTION

The present invention relates to an exhaust gas recirculating type diesel engine wherein part of the exhaust gas emitted into the exhaust system of a diesel engine is recirculated into the intake system of the engine. More particularly, the present invention relates to an exhaust gas recirculating type diesel engine having an improved piston structure for reducing problems, such as mechanical abrasion and chemical corrosion of mechanical parts and deterioration of lubricants, caused by micro particle impurities containing sulphuric acid components and generated as products of combustion in the diesel engine.

In a conventional gasoline engine, fuel and air are first mixed with each other, and then the resulting combustible gas mixture is supplied to a combustion chamber. Micro particles are usually not generated after the gas mixture is burnt. Even when part of the exhaust gas is recirculated from the exhaust system to the intake system in order to reduce the amount of oxides of nitrogen ($NO_x$) contained in the exhaust gas, no problems due to the generation of such small particles are encountered by such a gasoline engine.

Contrary to this, in a diesel engine, wherein fuel is injected into compressed air, small particles are generated when the engine is operating under a high load. However, in a conventional diesel engine, the maximum amount of fuel injection is limited so that the generation of small particles can be restricted to a level that does not prevent the diesel engine from being driven, although the output power of the diesel engine is rather lowered reduced from the maximum value. Recently, to comply with the requirements concerning the purification of exhaust gas, it has become necessary to apply exhaust gas recirculation to diesel engines to reduce emission of $NO_x$. However, when exhaust gas is recirculated in a diesel engine, the combustion in its combustion chamber may be incomplete, and as a result, a large amount of small particles may often be generated in a driving region wherein exhaust gas is recirculated. Diesel fuel contains more sulphur components than gasoline, and accordingly, small particles generated through the above-mentioned exhaust gas recirculation also contain a large amount of sulphur components. When these small particles containing a large amount of sulphur components pass through the narrow space between the piston rings and the cylinder wall, they are admixed with lubricant, which is thereby deteriorated. In addition, when lubricant admixed with such small particles reaches the valve drive system of the diesel engine, both mechanical and chemical ill effects may occur in various parts of the diesel engine, such as abrasion and corrosion in the valve mechanism, pistons, piston rings, and cylinder liners, and chemical deterioration of the lubricant. These problems have been a large barrier against applying exhaust gas recirculation to a diesel engine.

SUMMARY OF THE INVENTION

An object of the present invention is to provide an improved piston structure for an exhaust gas recirculating type diesel engine to reduce the transfer of injurious small particle material from the combustion chambers to the lubricant and the valve drive system.

Another object is to provide an improved piston and ring structure particularly adapted to reduce substantially the transfer of mechanically and chemically damaging particles down alongside the pistons in a diesel engine that has means for recirculating the exhaust gas.

In accordance with this invention, an annular groove is formed on the circumferential surface of each piston of an exhaust gas recirculating type of diesel engine. The location of each groove is near the top of the piston facing the combustion chamber, and a substantially annular ring that has an upper surface shaped to facilitate control of small particle material generated within the combustion chamber is engaged within the annular groove.

When the present invention is applied to a diesel engine that has an exhaust gas recirculating system, the problems caused by small particle material and present in any conventional exhaust gas recirculating diesel engine can be obviated. It should be noted, in any of the conventionally known diesel engines, no means has been discovered to overcome such problems, and accordingly, exhaust gas recirculation cannot effectively take place in any conventional diesel engine.

The substantially annular ring for preventing small particle material utilized in the present invention may comprise: a circumferential portion in the form of a short tube extending along the circumferential surface of the piston; and a radial portion connected to the circumferential portion and extending radially inward toward the central axis of the piston. The substantially annular ring may have an L-shaped or T-shaped cross-section, with its radial portion engaged within the annular groove formed on the piston.

It is preferable that a substantially annular ring utilized in the present invention be engaged within the annular groove of the piston under a low tension of between 0 and 0.7 kg, which tension is measured in accordance with the stipulations in Japanese Industrial Standard B 8132. The tension applied to the substantially annular ring of the present invention is much lower than that applied to a standard piston ring because the substantially annular ring of the present invention is intended to reduce the transfer of small particle material.

According to an embodiment of the present invention, the radial thickness of the tubular portion of the substantially annular ring for passage of small particle material past the piston gradually decreases from the thickness in the region where the radial portion and the circumferential portion intersect. According to this specially designed construction, the area of the substantially annular ring subjected to pressure in the combustion chamber can be enlarged. As a result, the substantially annular ring can have sufficient durability against the expanding operation by means of burnt gas of high temperature in the combustion chamber because the base of the circumferential portion is not excessively thin.

In another embodiment of the present invention, one or more additional annular grooves are formed on the circumferential surface of the piston between the previously described top annular groove, and the first piston ring engaging surface below the top annular groove.

The additional annular groove or grooves serve as means for attenuating pressure which is exerted on the substantially annular ring and which passes through the substantially annular ring because of the possible incomplete sealing ability of the substantially annular ring.

BRIEF DESCRIPTION OF THE DRAWINGS

Several embodiments of the present invention will now be explained with reference to the accompanying drawings, wherein:

FIG. 13 (A) is a diagram illustrating abrasion of cylinder liner installed in a conventional exhaust gas recirculating type of diesel engine;

FIG. 13 (B) is a diagram illustrating abrasion of cylinder liner installed in an exhaust gas recirculating type of diesel engine incorporating the present invention;

DETAILED DESCRIPTION OF THE INVENTION

Figure 1:
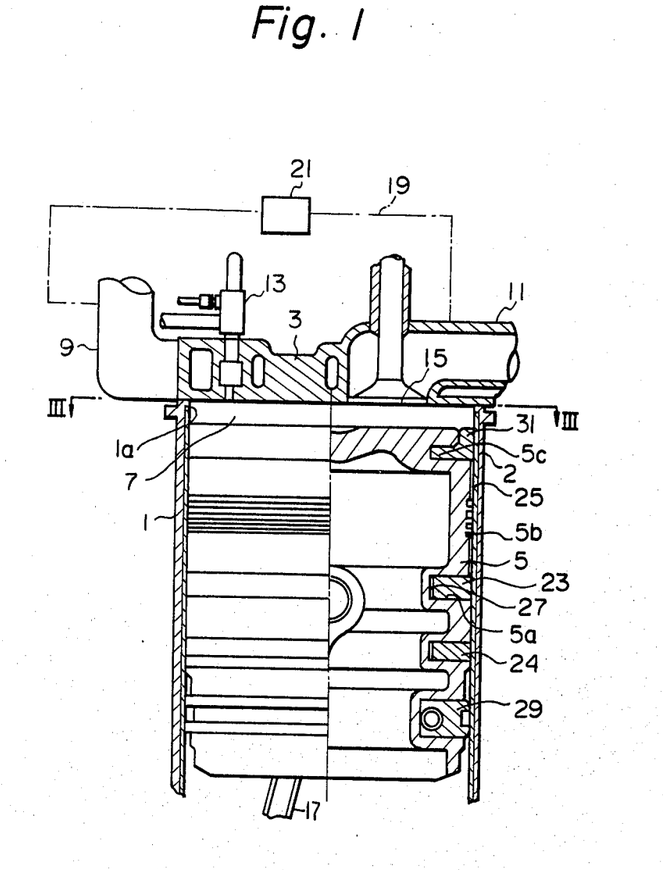
FIG. 1 is a schematic cross sectional elevational view of an exhaust gas recirculating type diesel engine showing a piston and ring structure according to the present invention.

In FIG. 1, wherein a cross sectional view of one cylinder in an exhaust gas recirculating type diesel engine according to the present invention is schematically illustrated, a cylinder liner 2 is fitted into a cylinder bore 1a formed in an engine block 1, and a cylinder head 3 is fixedly secured onto the engine block 1. A piston 5 is reciprocally movable within the cylinder liner 2, so that a combustion chamber 7 is formed by the cylinder liner 2, the cylinder head 3 and the top surface of the piston 5. The cylinder head 3 includes an intake port 9 for supplying a combustible gas mixture into the combustion chamber 7, an exhaust port 11 for discharging burnt exhaust gas from the combustion chamber 7, and an injection valve 13 for injecting fuel into the combustion chamber 7. An intake valve (not shown) is located where the intake port 9 opens into the combustion chamber 7, and an exhaust valve 15 is located where the exhaust port opens to the combustion chamber 7. The intake valve and the exhaust valve 15 are operated by means of a valve drive system (not shown) in synchronism with the movement of a crankshaft (not shown) connected to the piston 5 via a connecting rod 17. An exhaust manifold connected to the exhaust port 11 and an intake manifold connected to the intake port 9 communicate with each other by means of an exhaust gas recirculating system including a passage 19 and a control valve 21 used for controlling exhaust gas recirculation. The recirculation system has a conventional structure, so that part of exhaust gas in the exhaust system is recirculated into the intake system.

An annular ring groove 5a is formed on the circumferential surface of the piston 5, within which a compression piston ring 23 is engaged. As a result, a circumferential clearance 25 is formed between the piston 5 and the cylinder liner 2, and at the same time, a clearance 27 is also formed between the inside of the piston ring 23 and the bottom of the uppermost ring groove 5a.

The above-explained construction is substantially the same as that of a conventional exhaust gas recirculating type diesel engine. Such a conventional engine involves a disadvantage that burnt gas containing small particles essentially comprised of sulphur components generated in the combustion chamber 7 passes through the circumferential clearance 25 formed between the piston 5 and the cylinder liner 2 and then enters the clearance 27 formed between the piston ring 23 and the ring groove 5a. Since the piston ring 23 is vertically moved within the piston ring groove 5a during one cycle of the engine, the small particles contained in the burnt gas are successively transferred toward a piston ring 24, which is located beneath the uppermost piston ring 23, as the engine cycle takes place. In this transferring operation, some small particles invade a space facing the lower surface of the piston ring 23, and accordingly, the lower surface of the piston ring 23 is noticeably abraded due to the vertical movement of the piston ring 23. In addition, since small particles are successively transferred toward the lower piston ring 24 as explained above, the second compression piston ring 24 is similarly abraded. Furthermore, since an oil ring 29 located beneath the compression piston ring 23 and 24 is exposed not only to the small particles but also to lubricant applied thereto from the lubricating system of the engine, the oil ring may sometimes be subjected to more abrasion than the upper piston rings 23 and 24.

Small particles which are successively transferred toward the lower piston rings 23, 24 and 29, as explained above, are finally admixed with lubricant of the engine. The lubricant admixed with small particles is supplied to the valve drive system through a lubricating system (not shown), and simultaneously, the small particles contained in the lubricant also reach the valve drive system and cause the parts, such as cams, tappets and rocker arms, which constitute the valve drive system, to be abraded.

On the other hand, although some of the small particles entering the circumferential clearance 25 formed between the cylinder liner 2 and the piston 5 are deposited in the shallow grooves 5b formed on the circumferential surface of the piston 5, the remainder of the small particles are deposited on the inner surface of the cylinder liner 2 and the outer surface of the piston 5. The small particles deposited on the outer surface of the piston 5 abrade all the engaging surfaces of the piston 5 and the cylinder liner 2 as the piston 5 is moved vertically.

To avoid the abrasion of the piston rings caused by small particles contained in burnt gas in a conventional exhaust gas recirculating type engine, to eliminate the abrasion of the valve drive system caused by the admixing of such small particles with lubricant which is supplied to the valve drive system, and to obviate the abrasion of the engaging surfaces caused by the sliding movement of the piston which has small particles deposited on the circumferential surface thereof, the following special design is applied to the embodiment illustrated in FIG. 1. An annular groove 5c is formed at a location near the top of the piston 5, and a ring 31 is engaged within the annular groove 5c to prevent the transfer of small particle material from the combustion chamber 7, where it is generated to the piston ring engaging surface.

Figure 2:
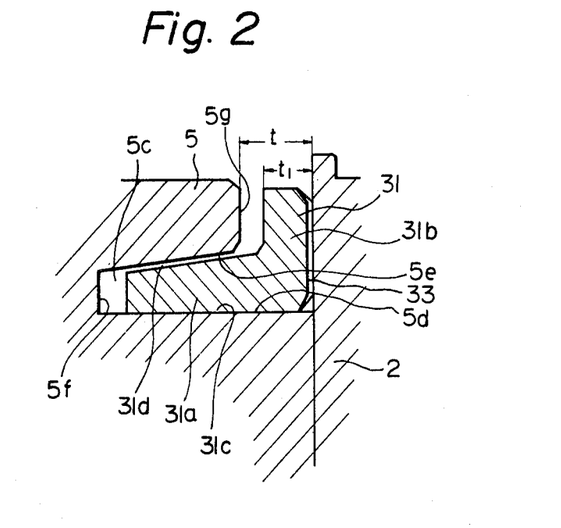
FIG. 2 is an enlarged cross-sectional view of a fragment of the piston and ring structure in FIG. 1.

Referring to FIG. 2, the annular groove 5c comprises a substantially horizontal bottom surface 5d, an upper surface 5e slightly inclined relative to the horizontal bottom surface 5d, and a vertical wall surface 5f connecting the bottom surface 5d and the upper surface 5e. The height of the annular groove 5c increases as a function of the distance from the center of the piston 5, and the radial length of the upper surface 5e of the annular groove 5c is shorter than that of the bottom surface 5d. The ring 31 for preventing small particle material has an L-shaped cross section comprising a radial portion 31a, the cross section of which corresponds to that of the annular groove 5c of the piston 5, and a short tubular circumferential portion 31b extending upward from the circumferentially outer perimeter of the radial portion 31a. More specifically, the bottom surface 31c of the radial portion 31a is flat, and the upper surface 31d of the radial portion 31a is inclined corresponding to the upper surface 5e of the annular groove 5c so that the thickness of the radial portion 31a converges toward the center of the piston 5. The area of the circumferential portion 31b which engages with the cylinder liner 2 is hardened by chrome plating or ferrite flame spraying. The thickness $t_1$ is much smaller than the clearance $t$ between the circumferential surface 5g of the upper surface 5e and the inner surface of the cylinder liner 2. The ring 31 is engaged within the annular ring 5c of the piston under a low tension of between 0 and 0.7 kg which tension is measured in accordance with the stipulations of Japanese Industrial Standard B 8130, and the ring 31 for preventing small particle material is made coaxial with the piston 5 by means of the cooperative centering action of the engaging upper surfaces 31d and 5e.

When such a ring 31, for preventing small particle material, having an L shape cross section is engaged with the portion near the top of the piston 5, small particles containing burnt gas are prevented from being transferred during the expansion stroke of the engine, and accordingly, they usually do not enter into the engaging surfaces of the cylinder liner 2 and the piston 5. In this case, burnt gas per se can pass through the narrow passage 33 formed between the portion 31b of the piston ring 31 and the inner surface of the cylinder liner 2, and in fact based on experimental tests, it has been confirmed that a gas flow exists at the location of the piston ring 23 (FIG. 1). However, small particles contained in the burnt gas enter the above-mentioned narrow passage 33 but cannot pass therethrough, and accordingly, they are deposited there. As a result, subsequent small particles find it harder to pass therethrough, and the amount of particles which reach the ring 23 (FIG. 1) becomes diminished.

Since the small particles are held back by the L shaped ring 31, sulphuric acid components contained in the small particles do not reach the ring 23 (FIG. 1). As a result, chemical corrosion of the cylinder liner 2 caused by the sliding movement of the ring 23 can be minimized. It should be noted that, since the ring 31 for preventing small particle material is engaged with the piston 5 under a low tension as explained above, the amount of small particles deposited on the outer surface of the preventing ring 31 which faces the narrow passage is small, and accordingly, the mechanical abrasion of the cylinder liner 2 due to the small particles deposited on the preventing ring is reduced. Furthermore, small particles clogged on the upper surface of the preventing ring 31 are exposed to the combustion chamber 7 (FIG. 1) and are burnt with burning gas in the combustion chamber when the engine is in a driving condition wherein the temperature of the burning gas is high. Therefore, the deposit of small particles on the top of the piston 5 is minimized.

Figure 3:
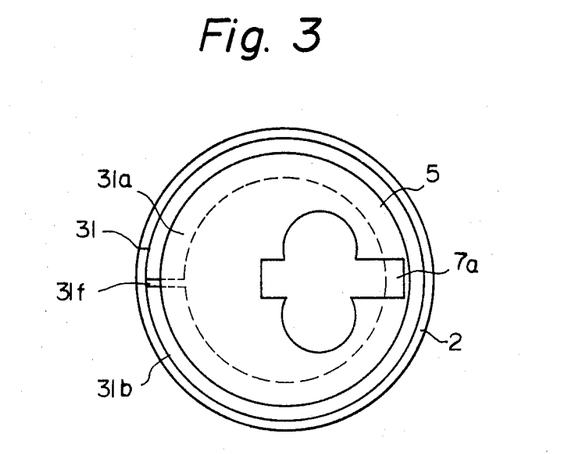
FIG. 3 is a plan view of the piston and ring structure taken along line III—III in FIG. 1.
Figure 9:
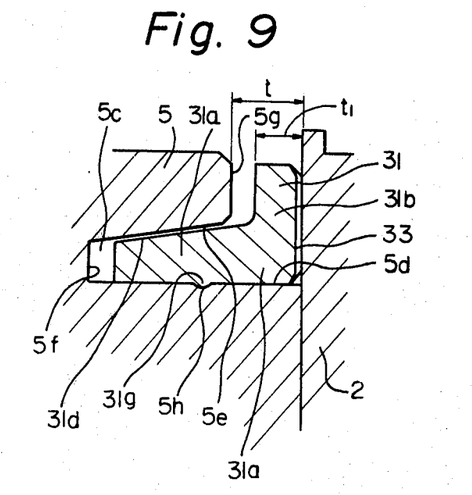
FIG. 9 is an enlarged cross-sectional view of still another embodiment.

When the top of the piston 5 illustrated in FIG. 1 has a clover shaped combustion chamber 7a formed thereon as illustrated in FIG. 3, it is preferable that the opening 31f of the preventing ring 31 be located farthest away from the clover shaped combustion chamber 7a where the thermal load is maximum, so that the blow-off of the burnt gas is prevented and so that the possibility that small particles may pass through the opening 31f of the preventing ring 31 with the burnt gas is lowered. In this case, as illustrated in FIG. 9, a suitable recess 5h may be formed on the bottom surface 5d of the annular groove 5c, and a projection 31g may be formed on the bottom surface 31c of the preventing ring 31, whereby the recess 5h and the projection 31g are engaged with each other in order to circumferentially position the preventing ring 31 at a predetermined location. In an alteration, it is possible that a projection (not shown) is formed on the surface 5d of the annular groove 5c, and a recess (not shown) is formed on the bottom surface 31c of the preventing ring 31, so that the recess and the projection are engaged with each other. The number of the projections and the recesses may be one or more and is set in accordance with the desired performance.

Figure 4:
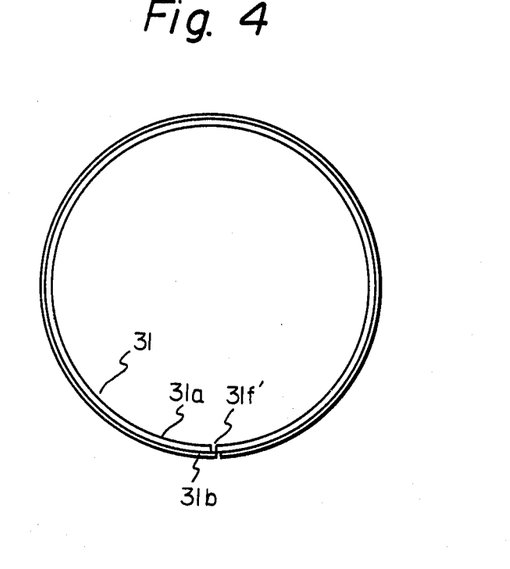
FIG. 4 is a plan view of a substantially annular ring for preventing circulation of small particle material.
Figure 5:
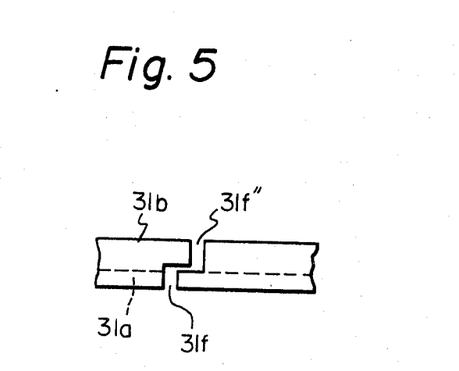
FIG. 5 is an enlarged elevational view of a fragment of the ring in FIG. 4.

Instead of the above-explained embodiments wherein the opening 31f of the preventing ring 31 is fixed at a certain location, the opening 31f of the preventing ring 31 may have an overlapping end structure as illustrated in FIGS. 4 and 5 so that small particles do not pass through the opening 31f with ease. More specifically, the ends 31f′ of the radial portion 31a of the preventing ring 31 are slightly displaced with respect to the ends 31f/41 of the circumferential portion 31b, so that a crank-shaped opening 31f is formed. The crank-shaped opening 31f prevents small particles from being easily passed therethrough.

Figure 6:
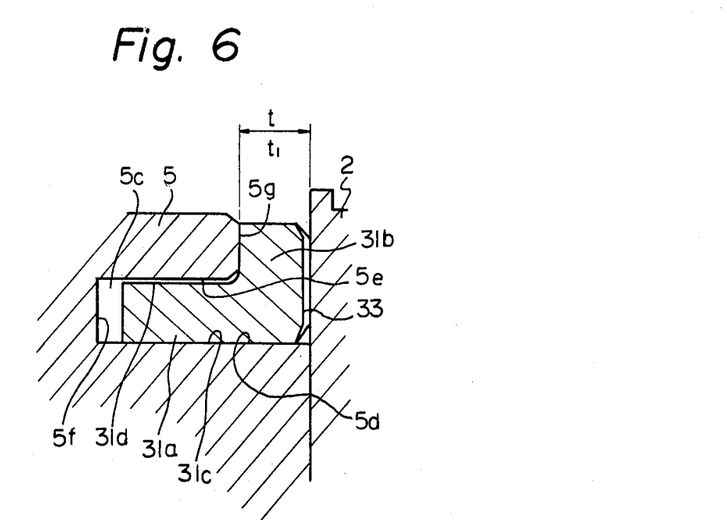
FIG. 6 is an enlarged fragmentary cross-sectional view of another embodiment of a piston and ring structure according to the invention.

An embodiment illustrated in FIG. 6 is different from that illustrated in FIG. 2 in that the thickness $t_1$ of the circumferential portion 31b of the preventing ring 31 is approximately equal to or slightly smaller than the clearance t between the circumferential surface 5g of the piston 5 and the inner surface of the cylinder liner 2. The upper surface 31d of the radial portion 31a of the preventing ring 31 and the upper surface 5e of the annular groove 5c are parallel to the bottom surfaces 31c and 5d, respectively. However, the upper surfaces 31d and 5e may be inclined as illustrated in FIG. 2. According to the embodiment illustrated in FIG. 6, advantages similar to those achieved by the above-explained embodiments can be obtained. In this embodiment, it is preferable that the preventing ring 31 be made of a material having a small coefficient of thermal expansion so that the adverse influence of thermal expansion can be reduced.

Figure 7:
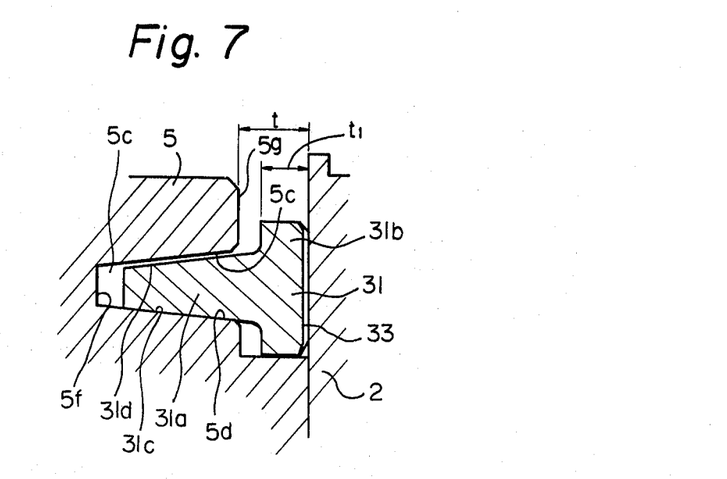
FIG. 7 is an enlarged cross sectional view of a further embodiment.

In an embodiment illustrated in FIG. 7, the circumferential portion 31b of the preventing ring 31 extends both upward and downward with respect to the radial portion 31a so that the preventing ring 31 has a T-shaped cross-section. In addition, the upper surface 31d and the bottom surface 31c of the preventing ring 31 are inclined in order to converge toward the center of the piston 5. The upper surface 5e and the bottom surface 5d of the annular groove 5c formed on the piston 5 are also included, so that the distance between them increases with increasing distance from the piston axis. Due to the engagements between the upper surfaces 31d and 5c and between the bottom surfaces 31c and 5d, the preventing ring 31 is retained coaxial with the piston 5. In addition, since the circumferential portion 31b of this embodiment is symmetrical relative to a central horizontal plane, it is unnecessary to orient the preventing ring 31 with a specific side facing upward while the ring is being fitted onto the piston, and therefore, the handling of the ring 31 is easy.

Figure 8:
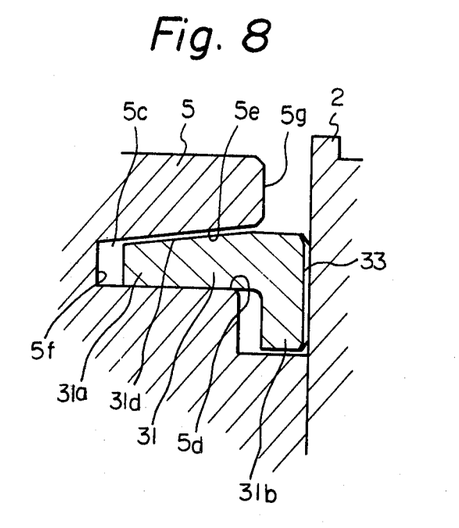
FIG. 8 is an enlarged cross sectional view of a still further embodiment.

In the embodiment illustrated in FIG. 8, a ring 31 for preventing small particle material has an L-shaped cross section and a construction similar to that illustrated in FIG. 2. However, in FIG. 8, the preventing ring 31 is so arranged that the circumferential portion 31b thereof extends downward. Some advantages similar to those of the embodiment in FIG. 2 can be achieved. However, in this embodiment, since the radial portion 31 does not face the combustion chamber 7 (FIG. 1), the advantage present in the embodiments illustrated in FIGS. 2, 7 and 9 cannot be expected because the burnt gas pressure does not exert radially outward pressure on the tubular circumferential portion 31b and the circumferential surface 5g of the piston 5, which would cause the tubular portion to narrow the narrow further passage 33 between the radial portion 31b and the cylinder liner 2, in order to further prevent the small particles from passing therethrough.

Figure 10:
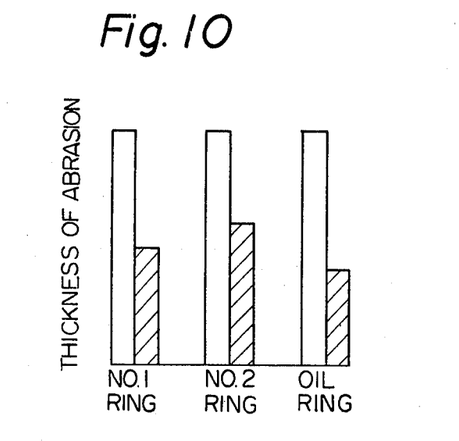
FIG. 10 is a chart illustrating advantages achieved by the present invention in decreasing abrasion of the thickness of the piston rings.
Figure 11:
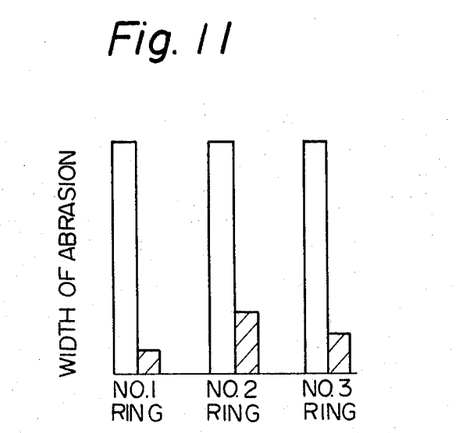
FIG. 11 is a chart illustrating advantages achieved by the present invention in decreasing abrasion of the width of the piston rings.
Figure 12:
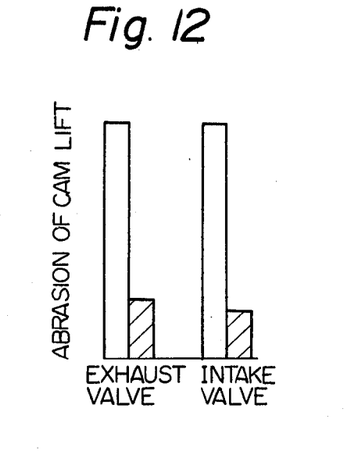
FIG. 12 is a chart illustrating advantages achieved by the present invention in decreasing abrasion of the cam lifters.

The advantages achieved by the embodiment illustrated in FIGS. 1 and 2 will now be explained with reference to FIGS. 10 through 12. In FIGS. 10 through 12, white bars indicate amounts of abrasion when the preventing ring of the present invention is not utilized, and the hatched bars indicate the amounts of abrasion when the preventing ring of the present invention is utilized. FIG. 10 illustrates the abrasion in thickness (T size) of the compression rings and the oil ring. FIG. 11 illustrates the abrasion in width (B size) of the compression rings and the oil ring. From FIGS. 10 and 11, it will be obvious that, according to the present invention, the amount of abrasion on the piston rings can be remarkably reduced. Furthermore, FIG. 12 illustrates the abrasion in cam lifters of the valve drive system. It will also be obvious that the amount of the abrasion on the cam lifters can be greatly reduced by means of the present invention.

Figure 13:
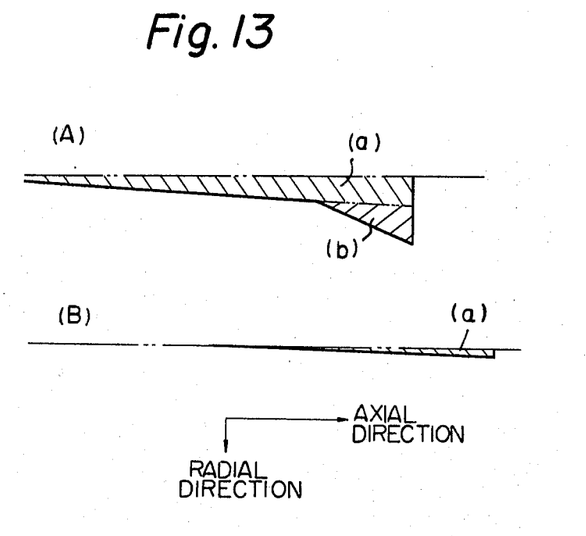

FIGS. 13(A) and 13(B) illustrate the abraded conditions of the surfaces of the cylinder liner after they were subjected to an endurance test. FIG. 13(A) illustrates the result obtained in a test without the preventing ring of the present invention, and FIG. 13(B) illustrates the result obtained in a test with the preventing ring of the present invention. In FIGS. 13(A) and 13(B), the abrasion denoted by (a) is caused by a mechanical abrasion generating mechanism, and the abrasion denoted by (b) is caused by a chemical corrosion generating mechanism. From FIGS. 13(A) and 13(B), it will be obvious that the abrasion of the cylinder liner can be decreased in accordance with the object of the present invention.

Figure 14:
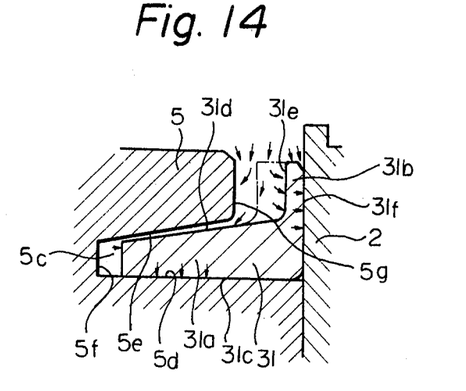
FIG. 14 is an enlarged cross sectional view of another embodiment.

To enhance the advantage achieved by the embodiments illustrated in FIGS. 2, 7 and 9 that the preventing ring 31 is expanded outward due to the burnt gas pressure so that the outer circumferential surface is pressed against the cylinder liner 2 and so that small particles are prevented from reaching the piston rings 23 and 24, it is preferable to provide sufficient space between the vertical circumferential surface 5g of the piston and the inner vertical surface 31e of the preventing ring 31. In FIG. 14, the thickness of the circumferential portion 31b of the preventing ring 31 is narrowed to increase the annular space between the piston 5 and the preventing ring 31.

Figure 15:
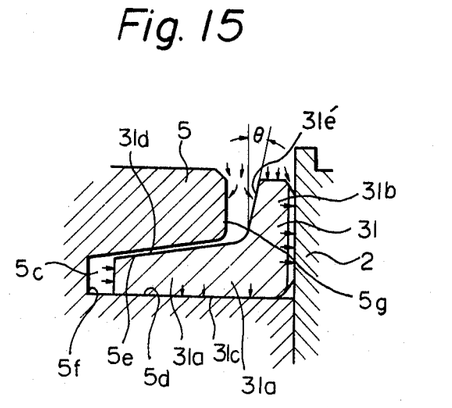
FIG. 15 is an enlarged cross sectional view of still another embodiment.
Figure 16:
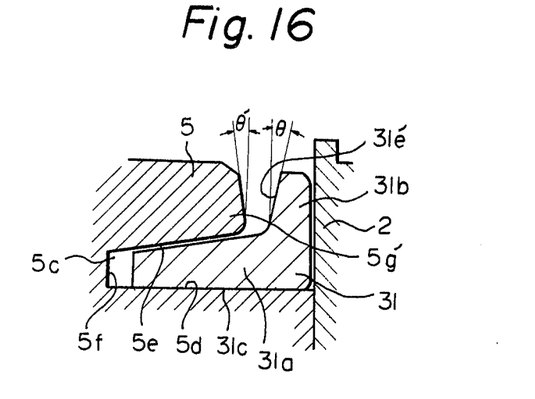
FIG. 16 is an enlarged cross sectional view of a still further embodiment.

However, when the circumferential portion 31b is made excessively thin, the circumferential portion 31b may melt or be broken when it is subjected to burnt gas having a high temperature. In an embodiment illustrated in FIG. 15, the thickness of the circumferential portion 31b of the proventing ring 31 is gradually decreased from the base, where it is connected to the radial portion 31a toward the top of the piston 5. In other words, instead of the vertical surface 31e in FIG. 14, an inclined surface 31e' intersecting a vertical line by an angle $\theta$ is formed, and accordingly, the area of the preventing ring 31 on which the pressure in the combustion chamber 7 (FIG. 1) is exerted is made sufficiently large, yet the durability of the preventing ring 31 is high because the thickness of the circumferential portion is not excessively thin. In the embodiment illustrated in FIG. 16, instead of the vertical surface 5g in FIG. 14, a surface 5g' inclined opposite to the inclined surface 31e' by an angle $\theta'$ against a vertical line is formed. Due to the inclined surfaces 5g' and 31e', a large space is formed therebetween.

Figure 17:
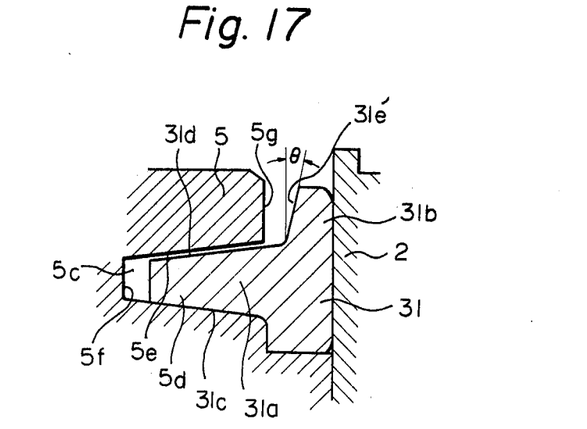
FIG. 17 is an enlarged cross sectional view of yet another embodiment.

In the embodiment illustrated in FIG. 17, a preventing ring 31 having a T shape cross section is used, and the upper circumferential portion 31 is inclined so that the thickness thereof is gradually decreased from the base to the top thereof.

Figure 18:
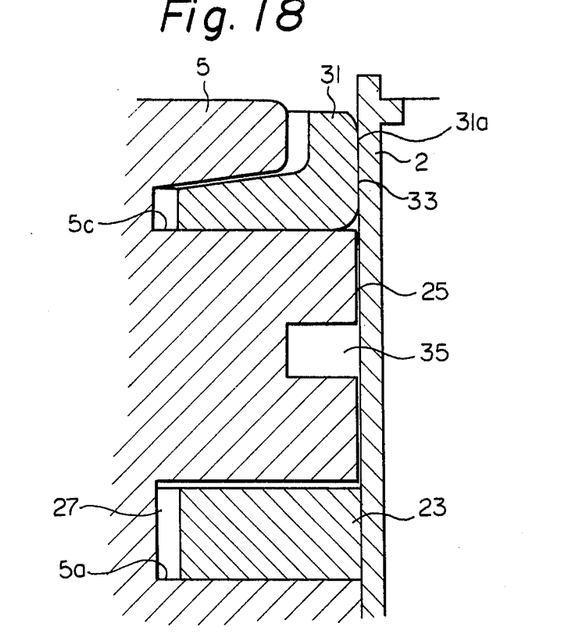
FIG. 18 is a cross sectional elevational view of a fragment of a piston and ring structure according to a further embodiment.
Figure 19:
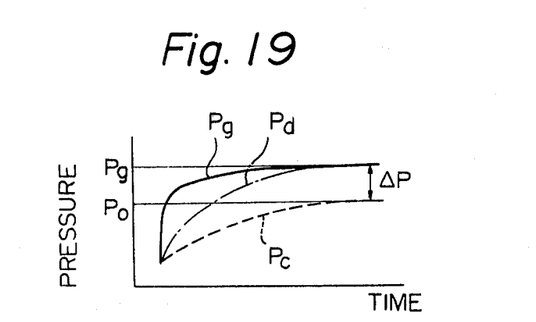
FIG. 19 is a graph illustrating changes in pressure on parts of the structure illustrated in FIG. 18.

As already explained above with reference to FIG. 1, there is a gas flow around the piston ring 23. In other words, it is very difficult to completely seal the pressure Pg exerted within the combustion chamber by means of the preventing ring 31, and accordingly, a very small amount of particles may move to the compression ring 23 through the narrow passage 33. In the embodiment illustrated in FIG. 18, an annular groove 35 is formed on the circumferential surface of the piston 5 located between the annular groove 5c within which the preventing ring 31 is engaged and the ring groove 5a within which the first compression piston ring 23 is engaged, so that a pressure attenuating chamber is formed. Due to the existence of such an attenuating chamber, the increase of the pressure Pc exerted on the compression piston ring 23 is delayed. More specifically, in FIG. 19, a solid line Pg denotes the pressure change in the combustion chamber during the expansion stroke, a dot and dash line Pd denotes the pressure change at a location just below the preventing ring 31 (FIG. 1). Since the pressure is throttled by means of the narrow passage 33, the increase of the pressure Pd is delayed, however, the pressure Pd is related to the pressure Pg. When the pressure attenuating chamber is formed, the pressure Pc exerted on the compressed piston ring 23 is delayed substantially as denoted by a broken line Pc, and since the time period of the expansion stroke is very short, the pressure Pc exerted on the compressed piston ring 23 is lower than that exerted within the combustion chamber 7 (FIG. 1) by $\Delta P$. As a result, even if the gas sealing capability of the preventing ring 31 is incomplete, small particles usually do not flow downward across the compression ring 23 because the pressure of the gas containing small particles is low. Thus, the abrasion of the compression piston rings 23 and 24 and the oil ring 29 is decreased, and the deterioration of the lubricant can be decreased.

Figure 20:
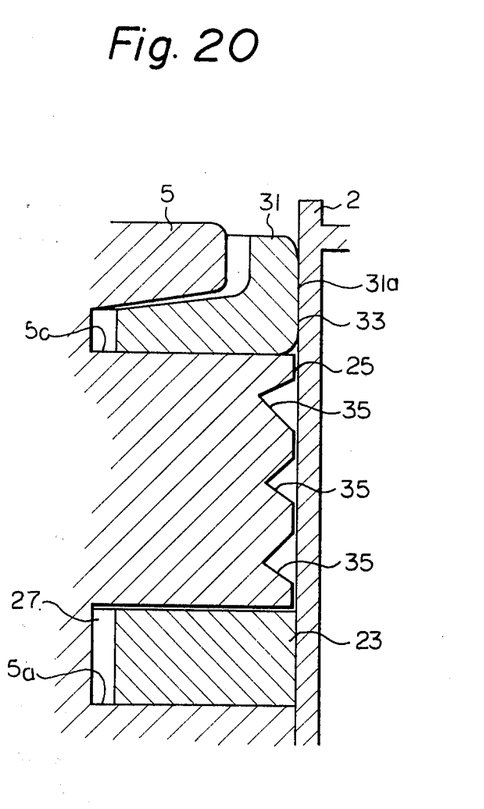
FIG. 20 is a cross sectional elevational view of a fragment of a still further embodiment.

The cross sectional shape of the annular groove 35 forming the pressure attenuating chamber may variously be altered; for example, as illustrated in FIG. 20, a triangular cross section can be applied. Furthermore, the number of the annular grooves 35 may be one or more.

We claim:

1. An exhaust gas recirculating type diesel engine having a cylinder with a cylinder liner, a cylinder head closing the top of the cylinder, a piston movable in the cylinder and comprising a circumferential surface and a top, the top defining with a cylinder liner and cylinder head a combustion chamber, a piston ring recess in the circumferential surface of the piston and a piston ring therein, an intake system for providing air to the combustion chamber, an exhaust system for leading exhaust material from the combustion chamber, and recirculation means to return a part of the exhaust material from the exhaust system to the intake system, wherein the improvement comprises:

an annular groove formed in the circumferential surface of the piston between said top and said piston ring recess and facing the cylinder liner; and a substantially annular ring engaged in the annular groove and comprising a radial portion extending generally radially inwardly into said groove, and a circumferential portion extending from the outer region of the radial portion longitudinally along the cylinder liner, said substantially annular ring serving as means to impede small particle material generated within the combustion chamber from moving to the region of the piston ring.

2. An exhaust gas recirculating type diesel engine according to claim 1, wherein said substantially annular ring has an L shape cross section, the circumferential portion of which is located near to said piston top relative to the radial portion thereof.

3. An exhaust gas recirculating type diesel engine according to claim 1, wherein said substantially annular ring has a T shape cross section, the circumferential portion of which is located at both said piston's top side and said piston's ring side relative to said radial portion.

4. An exhaust gas recirculating type diesel engine according to claim 2 or 3, characterized in that the thickness $t_1$ of said circumferential portion of said substantially annular ring for preventing small particle material located near to said piston top is sufficiently smaller than the radial clearance t between said cylinder liner and the outside surface of said piston adjacent to the inside of said circumferential portion of the annular ring, whereby a clearance is formed between the inside of said circumferential portion of said substantially annular ring and the outside of said piston when said substantially annular ring is engaged with said annular groove.

5. An exhaust gas recirculating type diesel engine according to claim 1 or 2, characterized in that, when said piston is cross sectioned along a plane including said central axis of said piston, said annular groove formed on said circumferential surface of said piston diverges from said central axis of said piston toward the circumferential surface of said piston, and said radial portion of said substantially annular ring converges from said circumferential portion to said central axis so as to correspond to said annular groove.

6. An exhaust gas recirculating type diesel engine according to claim 1 or 2, characterized in that said substantially annular ring is engaged within said annular groove of said piston under a low tension of between 0 and 0.7 kg, which tension is measured in accordance with the stipulations of Japanese Industrial Standard B 8032.

7. An exhaust gas recirculating type diesel engine according to claim 2 or 3, characterized in that the thickness of said circumferential portion of said substantially annular ring is gradually decreased from a portion, where said circumferential portion is connected to said radial portion, toward the piston top.

8. An exhaust gas recirculating type diesel engine according to claim 1 or 2, characterized in that at least one additional annular groove is formed on the circumferential surface of said piston located between said annular groove engaging with said substantially annular ring and said piston ring recess, so that at least one chamber for attenuating pressure is formed.

* * * * *

UNITED STATES PATENT AND TRADEMARK OFFICE
CERTIFICATE OF CORRECTION

PATENT NO. : 4,409,947
DATED : October 18, 1983
INVENTOR(S) : Hiromichi Yanagihara, et al.

It is certified that error appears in the above—identified patent and that said Letters Patent is hereby corrected as shown below: Title page, Change the Name of the Assignee from:

"Toyota Jidosha Kabushiki Kaisha" to

--Toyota Jidosha Kogyo Kabushiki Kaisha--.

Col. 1, lines 36 and 37, delete "rather lowered".

Col. 2, line 41, change "8132" to --8032--.

Col. 2, line 49, after "for" insert --preventing--.

Col. 4, line 54, change "ring" to --rings--.

Col. 5, line 57, change "8130" to --8032--.

Col. 6, line 63, change "31f" to --31f'--.

Col. 6, line 65, change "31f 41" to --31f"--.

Col. 8, line 40, after "31a" insert a --,--.

UNITED STATES PATENT AND TRADEMARK OFFICE
CERTIFICATE OF CORRECTION

PATENT NO. : 4,409,947
DATED : October 18, 1983
INVENTOR(S) : Hiromichi Yanagihara, et al.

It is certified that error appears in the above—identified patent and that said Letters Patent is hereby corrected as shown below:

ɔl. 9, lines 23 and 25, delete "compression".

Signed and Sealed this

First Day of May 1984

[SEAL]

Attest:

Attesting Officer

GERALD J. MOSSINGHOFF

Commissioner of Patents and Trademarks